United States Patent [19]

Nile et al.

[11] Patent Number: 5,399,400
[45] Date of Patent: Mar. 21, 1995

[54] ELASTOMERIC ARTICLES

[75] Inventors: Jeffery G. Nile, Alliance; Stanley J. Gromelski, Canton, both of Ohio

[73] Assignee: Smith & Nephew, Inc., Itasca, Ill.

[21] Appl. No.: 928,544

[22] Filed: Aug. 13, 1992

Related U.S. Application Data

[63] Continuation of Ser. No. 725,189, Jul. 3, 1991, abandoned.

[51] Int. Cl.$^6$ .................... C08L 7/02; C08L 27/18; C08J 5/02
[52] U.S. Cl. .................... 428/36.8; 428/220; 525/199; 523/122; 524/520; 524/501; 604/349; 2/168
[58] Field of Search ............ 525/199; 524/520, 501; 428/36.8, 220; 523/122

[56] References Cited

U.S. PATENT DOCUMENTS

| | | | |
|---|---|---|---|
| 2,681,324 | 6/1954 | Hochberg | 524/501 |
| 2,718,452 | 9/1955 | Lontz | 525/199 |
| 3,002,938 | 10/1961 | Gagne | 525/199 |
| 3,019,206 | 1/1962 | Robb | 525/199 |
| 3,223,676 | 12/1965 | Rucker | 260/41.5 |
| 3,772,236 | 11/1973 | Scheemda | 524/507 |
| 3,940,455 | 2/1976 | Kaufman | 525/199 |
| 4,596,839 | 6/1986 | Peters | 525/199 |
| 4,596,855 | 6/1986 | Stewart | 525/199 |
| 4,963,623 | 10/1990 | Miller et al. | 525/237 |
| 5,091,442 | 2/1992 | Milner | 523/122 |

OTHER PUBLICATIONS

Derwent Publications Abstract of Japanese Patent Application 1,240,554A. Class A14 AN89-321394 Sep. 1989.

*Primary Examiner*—Carman J. Seccuro, Jr.
*Attorney, Agent, or Firm*—Rosenman & Colin

[57] ABSTRACT

A thin walled article such as a surgical glove is formed from a blend of an elastomer as natural rubber and polytetrafluoroethylene.

10 Claims, No Drawings

ELASTOMERIC ARTICLES

This application is a continuation of application Ser. No. 07/725,189, filed Jul. 3, 1991, now abandoned.

The present invention relates to thin walled elastomeric articles, compositions for forming the articles and processes for their manufacture.

Rubber articles such as surgeons' gloves, condoms, sheaths and alike articles for application to a body part are normally provided with one or more thin walled portions to enable the article to fit conformably and comfortably over a body part e.g. a hand or a penis and also to allow the wearer to retain a sense of "feel" through the wall or walls of the article. An important function of these rubber articles is to provide a barrier to materials such as body fluids, bacteria and viruses and thus prevent the passage of these materials to the wearer or from the wearer to another person. It has been found, however, that thin walled rubber articles such as surgeons' gloves may tear or puncture when exposed to undue stress, thereby destroying the barrier properties thereof. This may occur, for example, during donning or flexing of the gloves or handling instruments with a rough surface or sharp projection while wearing the gloves.

The present invention attempts to overcome these problems by providing thin walled articles made of a material which has improved tear strength.

Accordingly the present invention provides a thin walled article formed of an elastomeric material comprising a blend of an elastomer and polytetrafluoroethylene.

A thin walled article as used herein is an article having a wall portion which has a average thickness of suitably less than 500 $\mu$m, favourably less than 350 $\mu$m and preferably less than 250 $\mu$m. Such an article can have a wall portion which has an average thickness of suitably greater than 25 $\mu$m, favourably greater than 50 $\mu$m and preferably greater than 75 $\mu$m.

Thin walled articles of the invention include gloves e.g. for medical or surgical pruposes, such as surgeons' gloves or examination gloves, condoms and sheaths, e.g. penile sheaths for incontinence devices.

The improved tear resistance of a thin walled article of the invention can provide the wearer with added confidence that the barrier properties of the article will be maintained during use.

An elastomer as used herein is a material which has an elastic recovery of at least 60%, favourably an elastic recovery of at least 80% and preferably an elastic recovery of at least 90% after being stretched by at least 100% at 20° C.

The elastomer can be a synthetic rubber. Suitable synthetic rubbers include polyurethanes, Cis-1,4 polyisoprene, butadiene homopolymer or copolymers thereof with styrene or acrylonitrile, isobutylene polymers for example butyl rubber and ethylene propylene copolymers.

The elastomer, however, is favourably natural rubber and preferably a cured or vulcanised natural rubber.

The elastomeric material used in the invention comprises a blend of elastomer and polytetrafluoroethylene abbreviated hereinafter as PTFE.

The blend can suitably contain at least 1 part by weight of PTFE, favourably at least 2 parts by weight of PTFE and can preferably contain at least 3 parts by weight of PTFE per hundred parts by weight of elastomer.

The blend can also suitably contain not more than 30 parts by weight of PTFE. Favourably not more than 20 parts by weight of PTFE and can preferably contain not more than 15 parts by weight of PTFE per hundred parts by weight of elastomer, for example 3 to 15 parts by weight of PTFE per hundred parts by weight of elastomer.

Thin walled gloves with improved tear strength have been found using blends containing 4 to 10 parts by weight of PTFE per hundred parts by weight of elastomer such as natural rubber.

Thin walled articles of the invention can conveniently be formed from a blend of elastomer and PTFE components in aqueous dispersion or latex form.

In another aspect therefore present invention provides a composition for forming thin walled articles of the invention which comprises a blend of an elastomer latex or aqueous dispersion thereof and an aqueous dispersion of PTFE.

Elastomer latices and dispersions suitable for forming thin walled articles of the invention such as gloves, condoms and sheaths are given in "Polymer Latices and their Applications" edited by K. O. Calvert and published in 1982 by Applied Science Publishers Ltd., the disclosure of which is incorporated herein.

Favoured elastomer latices are natural rubber latices. A preferred latex of this type is a prevulcanised natural rubber latex. Such a latex may be a conventional latex e.g. as described in the above Calvert reference. The stability, curing rate or solids content of the latex, however, may be adapted according to the article properties or a process for its manufacture.

The aqueous dispersion of PTFE can suitably contain PTFE particles of less than 1 $\mu$m in size and preferably 0.6 $\mu$m in size for example 0.05 to 0.5 $\mu$m in size.

An apt aqueous dispersion of this type is known as Teflon PTFE Grade B made by Du Pont. This dispersion has a solids content of 61% and a pH of 8.5. The amount of each latex or dispersion in the composition can be adjusted to obtain a dried blend with the chosen natural rubber—PTFE ratios.

The blend composition can optionally contain additives such as bactericides, viricides, colouring agents or fillers, viscosity modifiers, polymer stabilisers etc. to enhance the properties of the formed article or the process for their formation.

In further aspect the present invention provides a process for forming a thin walled article of the invention in which the article is formed from a composition of the invention.

A favoured process of the invention for forming a thin walled article such as a glove, condom or sheath comprises a dipping process.

The dipping process can be a conventional process for forming thin walled articles of the above type.

Suitable dipping processes are given in the Calvert reference hereinbefore mentioned in relation to elastomer latices of dispersion.

In the dipping process a former for the thin walled article is dipped into one or more baths containing a blend of the rubber latex and PTFE dispersion and the coated former dried to form the article which is then stripped from the former. In a dipping process for gloves, the former is usually preheated and precoated with a coagulant before being dipped into the bath containing the latex blend.

After the coated former has been air dried, it can be dipped into a tank of hot water to leach out water soluble materials.

When the rubber latex used in the process contains vulcanising agents or is a prevulcanised rubber latex the coated former can be heated for a period of time to "cure" the rubber. The article can then be stripped from the former. A glove article, however, is normally provided with a lubricant such as starch powder to act as a donning aid before it is stripped from the former.

The formed article can then be packaged individually or in the case of gloves as a pair and if necessary sterilised within the package by a conventional dry sterilising method. A sterile thin walled article such as a glove or pair of gloves within a bacteria proof package is therefore part of the invention.

The invention will now be illustrated by the following examples.

EXAMPLE 1

Rubber gloves were made by a conventional dipping process using a heated glove former precoated with coagulant and a dipping bath containing a blend of prevulcanised rubber latex (solids content 41%) and PTFE aqueous dispersion (Teflon PTFE Grade B) available from Du Pont containing PTFE particles of 0.05 to 0.5 $\mu$m in size and of a solid content 61%.

The ratio of natural rubber latex to PTFE dispersion in the bath was adjusted to obtain a dried blend with natural rubber to PTFE ratio of 100:4.

After dipping, the latex coated former was air dried for 1 to 2 minutes, dipped into a tank of hot water (temperature 70° C.) for 2 minutes to leach out any water soluble materials and then heated to 110° C. for about 20 minutes to cure the rubber. After cooling the outer surface of the glove was dusted with corn starch powder and stripped from the former.

Glove samples of this example had an average wall thickness in the region of 180 $\mu$m. When tested for tear resistance, it was found that the glove samples exhibited values which were double that obtained from similar control rubber gloves formed from prevulcanised natural rubber latex only.

EXAMPLES 2 and 3

Rubber gloves were formed in the same manner to Example 1 except that the ratio of prevulcanised natural rubber latex to PTFE dispersion in the bath was adjusted to obtain a ratio of natural rubber to PTFE in the dried blend of 100:7 (Example 2) and 100:10 (Example 3) respectively.

Glove samples of Examples 2 and 3 when tested for tear resistant properties both exhibited values which were double that obtained for a similar natural rubber control glove.

We claim:

1. A thin walled article having an average thickness of less than 500 $\mu$m formed from an elastomeric material comprising a blend of elastomer and an aqueous dispersion of polytetrafluoroethylene, in which the elastomer is natural rubber.

2. An article according to claim 1 which is in the form of a surgical or medical glove.

3. An article according to claim 1 which is in the form of a sheath or condom,

4. An article according to claim 1 in which the natural rubber is a cured or vulcanised rubber.

5. An article according to claim 1 in which the blend contains at least 2 parts by weight of polytetrafluoroethylene per hundred parts of elastomer.

6. An article according to claim 5 in which the blend contains not more than 30 parts by weight of polytetrafluoroethylene per hundred parts by weight of elastomer.

7. An article according to claim 1 in which the elastomer is a prevulcanised natural rubber.

8. An article according to claim 1 having an average thickness of less than 350 $\mu$m.

9. An article according to claim 1 having an average thickness of less than 250 $\mu$m.

10. An article according to claim 1 which additionally contains an effective amount of a bactericide, a viricide or a coloring agent.

* * * * *